United States Patent [19]

Ornter et al.

[11] Patent Number: 5,033,849
[45] Date of Patent: Jul. 23, 1991

[54] ATOMIZING DEVICE OF HIGH-MELTING METAL

[75] Inventors: Hugo Ornter, Hoefen; Peter Wilhartitz, Ehenbichl, both of Austria; Jiri Dolezal, Skolska, Czechoslovakia; Robert Hlavac, Horni Pocernice; Vaclav Sychra, Jaselska; Püschel, Jana Vrby, all of Czechoslovakia

[73] Assignees: Metallwerk Plansee GmBH, Reutte/Tirol, Austria; University of Prague Institute of Chemical Technology, Prague, Czechoslovakia

[21] Appl. No.: 460,271

[22] Filed: Jan. 2, 1990

[30] Foreign Application Priority Data

Jan. 4, 1989 [CS] Czechoslovakia ............ PV00075-89

[51] Int. Cl.$^5$ .................................... G01N 21/74
[52] U.S. Cl. .................................... 356/312; 356/244
[58] Field of Search ................... 356/311, 312, 244

[56] References Cited

U.S. PATENT DOCUMENTS

| 4,204,769 | 5/1980 | Lerschmacher et al. | 356/312 |
| 4,407,582 | 10/1983 | Woodriff | 356/312 |

FOREIGN PATENT DOCUMENTS

| 174728 | 7/1978 | Czechoslovakia. | |
| 2225421 | 5/1982 | Fed. Rep. of Germany. | |
| 3327698 | 2/1985 | Fed. Rep. of Germany | 356/312 |
| 2924123 | 4/1985 | Fed. Rep. of Germany. | |
| 3534417 | 4/1987 | Fed. Rep. of Germany. | |

*Primary Examiner*—F. L. Evans
*Attorney, Agent, or Firm*—Morgan & Finnegan

[57] ABSTRACT

The invention relates to an atomizing device of high-melting metal for an improved cost and precision of analysis in flameless atomic absorption spectroscopy which is heated by the direct passage of current. The atomizing device comprises of an upper and lower strip-shaped sheet metal part, placed on top of each other, each having a semi-cylindrical center section which form a hollow-cylindrical cuvette with lateral current lead-ins. The current lead-ins of the upper part extend over the entire length of the cuvette, whereas the current lead-ins of the lower part extend only across the end sections of the cuvette.

8 Claims, 2 Drawing Sheets

ATOMIZING DEVICE OF HIGH-MELTING METAL

BACKGROUND OF THE INVENTION

1. Field Of The Invention

The invention relates to an atomizing device of high melting metal for flameless atom absorption spectroscopy.

2. Description Of Related Art

In flameless atomic absorption spectroscopy, the sample to be analyzed is placed in a cuvette, usually tube-shaped, of graphite, and sometimes of high-melting metals such as tungsten or molybdenum. The sample is heated abruptly by passing electrical current through it. The sample is atomized into an atom cloud in which the elements of the sample to be analyzed are present in an atomic state. This atom cloud is penetrated by an analysis light beam corresponding to the resonance lines of the element to be analyzed. The degree of absorption of the analysis light beam gives an indication of the quantity of the analyzed element. In order to permit precise analysis of the sample, it is necessary to achieve the greatest possible uniformity of cuvette temperature over space and time at the exact moment of atomization in order to avoid matrix effects. Matrix effects can come about because compounds of the analyzed samples or the element to be analyzed with the cuvette material can be stable in zones of lower temperature. This causes a falsification of the analysis result, or at least a reduction in measurement sensitivity.

A design feature which in the past has proven effective to achieve an improved sensitivity of measurement and precision of the analysis is the use of a separate interior carrier element to carry the sample, usually situated inside the cuvette, which is primarily intended to have a certain retarding effect on the heat build-up in the sample area, and thereby an isothermal atomization.

For example, the patents DE-PS 29 24 123 and DE-PS 22 25 421 describe such specialized devices for flameless atomic absorption spectroscopy, which are equipped with a separate interior carrier element.

This special design of an atomizing device has significant advantages with respect to the precision of the analysis. However, the cost of the separate interior carrier element is of about the same order of magnitude as the cost of the cuvette itself and thus raises the total cost of the analysis significantly.

Another feature that has proven effective for achieving a certain retarding effect in atomizing devices in the heating of the cuvette through lateral current lead-ins from the ends.

U.S. Pat. No. 4,407,582, for instance, describes a graphite cuvette where the heating current is exclusively supplied at the ends of the cuvette via Y-shaped contact pieces or a slotted sleeve that makes contact with specially raised sections of the cuvette. With such a design, it is possible to achieve similar properties as with an atomizing device having separate interior carrier elements. However, this design has only proven effective when using graphite as a cuvette material and, due to the specific electrical and thermal properties of graphite, only for cuvettes of especially small dimensions.

The Czechoslovakian patent application 174 728, describes an atomizing device of high-melting metal such as tungsten, molybdenum or tantalum. The device consists of a tubular cuvette with lateral current lead-ins situated parallel with the axis of the tube. It is formed by two strip-shaped sheet metal parts with a semi-cylindrical center portion, gripped in cooled clamping devices at the lateral current lead-ins.

The disadvantage of this type of atomizing device is that it is not possible to achieve a constant temperature distribution over the entire cross-section of the cuvette due to the large heat drain by way of the cooled clamping devices. Moreover, this design requires a separate interior carrier element as well, in order to bring about the desired retardation effect in the heat build-up in the sample area.

The German disclosure document DE-OS 35 34 417 describes an atomizing device of graphite in which the current lead-ins form one unit with the cuvette. In the preferred embodiment, the current lead-ins are equipped with openings in the direction of the cuvette axis which reduce the cross-sectional area. In this manner, a heat drain by way of the cooled clamping devices is largely avoided. But even with this atomizing device it is not possible to achieve a retardation effect in the heat build-up in the sample area. In order to achieve satisfactory precision of the analysis, a separate sample carrier element in the form of a crucible has to be used here as well, which is heated independently of the heating of the cuvette.

SUMMARY OF THE INVENTION

The invention relates to an atomizing device of high melting metal for flameless atomic absorption spectroscopy. The device is heated by a direct passage of current and comprises a hollow-cylindrical cuvette with current lead-ins situated laterally in parallel with the cylinder axis. The atomizing device is formed by upper and lower strip-shaped cylindrical sheet-metal parts, each with a semi-cylindrical center portion placed on top of each other, which forms the hollow-cylindrical cuvette with lateral current lead-ins.

The invention is based on the objective of designing an atomizing device for flameless atomic absorption spectroscopy in such a manner that the best possible temperature uniformity over space and time is achieved at the exact moment of atomization, and thus a high precision of the analysis, without requiring separate additional devices such as interior carrier elements or crucibles.

DETAILED DESCRIPTION OF THE INVENTION

The invention relates to an atomizing device of high melting metal for flameless atomic absorption spectroscopy. The device is heated by a direct passage of current and comprises a hollow-cylindrical cuvette with current lead-ins situated laterally in parallel with the cylinder axis. The atomizing device is formed by upper and lower strip-shaped cylindrical sheet-metal parts, each with a semi-cylindrical center portion placed on top of each other, which forms the hollow-cylindrical cuvette with lateral current lead-ins.

The current lead-ins of the upper sheet-metal part extend over the entire length of the cuvette while the current lead-ins of the lower sheet-metal part extend only over the end sections of the cuvette.

The invention provides a certain retardation effect, which is brought about in the sample area, so that at the exact moment of atomization, an excellent uniformity of temperature in space and time is achieved over the length of the cuvette. This leads to an isothermal atomization, in which matrix effects are to a large extent excluded. The precision of the analysis corresponds at least to that which can be reached with atomizing devices equipped with separate interior carrier elements or crucibles. Since the design of the atomizing device according to the invention makes it possible to do without these separate interior carrier elements or crucibles, analysis costs are much more favorable and the precision of the analysis is substantially improved.

The lower part with the sample area, which is as a rule equipped with a trough, is designed so that the current lead-ins extend only over the end sections of the cuvette, a further elimination of matrix effects can be achieved which is even better than in atomizing devices having separate interior carrier elements or crucibles.

In particularly preferred designs according to the invention, the current lead-ins of the second part are slotted in parallel with the longitudinal cuvette axis, or the center section of the current lead-ins is removed.

In adapting the cuvette to specialized analysis tasks, it can be of advantage to equip the current lead-ins of the first part with holes in the area of the center section of the cuvette, running parallel with the longitudinal cuvette axis.

Suitable materials for the atomizing device are e.g. tungsten, molybdenum or tantalum; tungsten in particular has proven effective since it has the highest melting point.

In order to prevent warping of the atomizing device at the high temperatures necessary for atomization of the sample, it is advantageous to reinforce the semi-cylindrical center sections of the two sheet-metal parts by means of stamped-in ridges near the edges.

Figure 1:
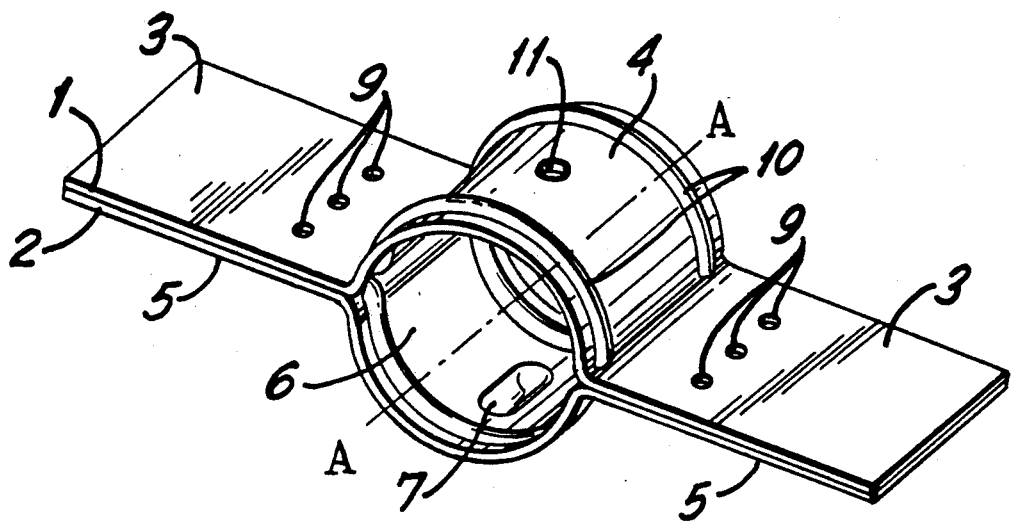
FIG. 1 shows in perspective view, one preferred embodiment of the disclosed atomizing device comprising parts placed on top of each other.
Figure 2:
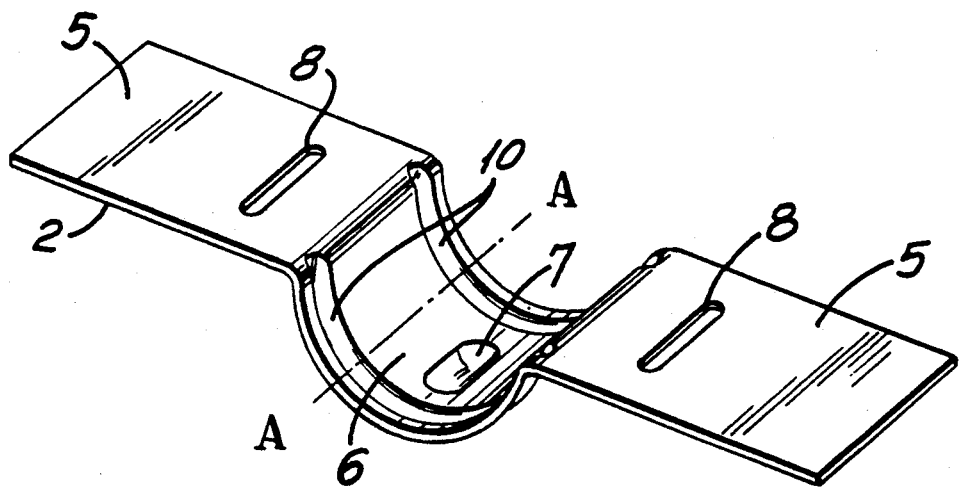
FIG. 2 shows in perspective view, one preferred embodiment of the lower part of the atomizing device.

FIG. 1 shows an atomizing device according to the invention, ready to be installed, comprising of an upper part 1 and a lower part 2 placed on top of each other. Further details of the lower part 2 can be viewed in FIG. 2.

The upper and lower parts of the atomized device comprise two strip-shaped sheet metal parts of equal width, made of tungsten with a thickness of 0.127 mm. Each part is fitted with a semi-cylindrical bulge 4 and 6 respectfully, at their center section. The hollow cylindrical cuvette is formed by a mirror-image placement of the upper part and lower part on top of each other. The upper and lower parts are loosely placed on top of each other and are gripped between cooled clamping devices (not shown) with their current lead-ins 3 and 5. The tightness of the hollow cylindrical cuvette required for atomization is achieved by means of sufficient clamping pressure of the clamping device and correspondingly precise tolerances of the upper and lower sheet metal parts. The upper part of the atomizing device has a circular opening 11 at the center of the semi-cylindrical cuvette section for introducing sample material. The lower part 2 of the atomizing device is the sample carrier area which has a built-in trough 7 at the center of the semi-cylindrical cuvette section, into which the sample material is inserted. The edge areas of the cuvette are fitted with enforcing ribs 10 in order to improve the warp resistance of the cuvette at the high temperatures required for atomization.

The lower part of the atomizing device has symmetrical slots 8 in the current lead-ins close to the transition to the semi-cylindrical cuvettes section, which run parallel with the cylinder axis A—A. These slots, which can be put in by means of a laser, restrict the current path of the current lead-ins in the end areas of the semi-cylindrical section to narrow bridges. In this manner, the heating of the lower part initially occurs at the ends of the semi-cylindrical section only. Only after the electrical resistance in the end areas has risen due to the increased temperature, the center area of of the semi-cylindrical section is also heated up by means of the direct passage of current.

The retardation effect in the heat build-up which is achieved in this manner is in the range of milliseconds. In contrast, the heat build-up of the semi-cylindrical section of the upper part occurs simultaneously over the entire length of the cuvette. Only the openings 9 located in the current lead-ins of the upper part, in parallel with the cylinder axis A—A, result in a certain control of current flow, which in certain cases leads to another improvement in the analysis conditions.

It is only through this special, differentiated heating of the upper and lower parts that a uniformity of temperature over time is achieved at the exact moment of atomization, extending over the entire length of the cuvette, so that isothermal atomization becomes possible, leading to very precise results.

Figure 3:
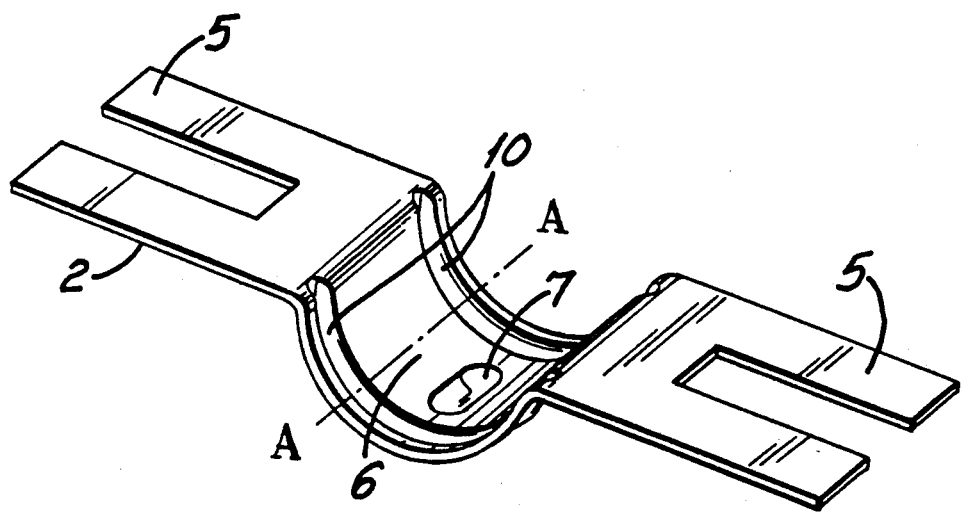
FIG. 3 shows one preferred embodiment of the lower part of the atomizing device.

FIG. 3 shows another advantageous design of the lower part of the atomizing device, in which the center section of the current lead-ins has been removed, e.g. by stamping. This design provides the heating of the semi-cylindrical section from the ends.

Corresponding with the Figures, the atomizing device is designed such that the current lead-ins of the upper part extend over the entire length of the cuvette, whereas the current lead-ins of the lower part extend only across the end sections of the cuvette. This design of an atomizing device permits the best results.

Figure 4:
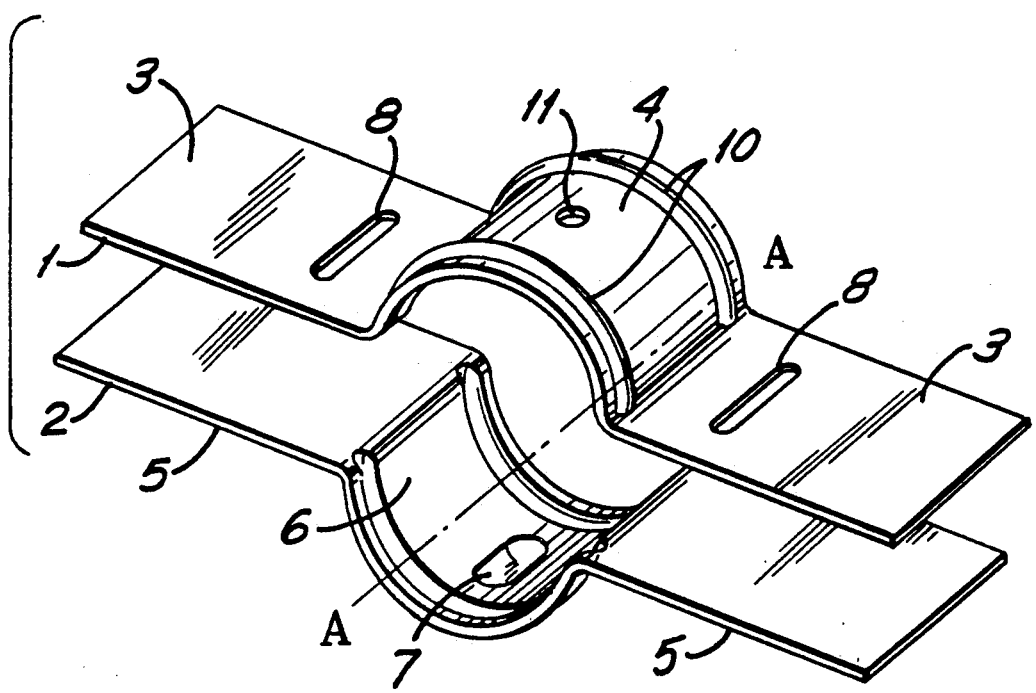
FIG. 4 shows in perspective view another preferred embodiment of the atomizing device.

The atomizing device can also be designed such that the current lead-ins of the lower part extend over the entire length of the cuvette, whereas the current lead-ins of the upper part extend only across the end sections of the cuvette. Such a configuration is depicted in FIG. 4, wherein like numerals refer to like elements as discussed for FIGS. 1-3 above. An atomizing device designed in this manner will also give a precise analysis, at least as good as that of atomizing devices with separate interior carrier elements or crucibles.

We claim:

1. An atomizing device of high melting metal, for flameless atomic absorption spectroscopy, adapted to be heated by a direct passage of current, comprising a hollow cylindrical cuvette with lateral current lead-ins situated parallel to the cylinder axis, that extend across the end sections of the cuvette; an upper strip-shaped sheet metal part of said hollow cylindrical cuvette with lateral current lead-ins, comprising a semi-cylindrical bulge, two current lead-ins which extend over the entire length of the cuvette and a circular opening at the center of said semi-cylindrical bulge; and a lower strip-shaped sheet metal part of said hollow cylindrical cuvette with lateral current lead-ins, comprising a semi-cylindrical bulge and two current lead-ins which extend only over the end sections of the length of the cuvette.

2. An atomizing device according to claim 1, further comprising a built in trough at the center of said semi-cylindrical bulge of said lower strip-shaped sheet metal part, so as to carry the sample to be analyzed.

3. An atomizing device according to claim 1, wherein the current lead-ins of the lower part are fitted with symmetrical slots close to the transition to said semi-cylindrical bulge, said symmetrical slots running parallel with the longitudinal axis of the cuvette.

4. An atomizing device according to claim 1, wherein the center section has been removed from the current lead-ins of said lower part.

5. An atomizing device according to claim 1, wherein the current lead-ins of said upper part are fitted with openings in the area of the center section of the cuvette, running parallel with the longitudinal axis of the cuvette.

6. An atomizing device according to claim 1, wherein tungsten is used as the high-melting metal.

7. An atomizing device according to claim 1, wherein the semi-cylindrical center section of the two sheet-metal parts are reinforced near the edges by means of stamped-in ribs.

8. An atomizing device of high melting metal, for flameless atomic absorption spectroscopy, adapted to be heated by a direct passage of current, comprising a hollow cylindrical cuvette with lateral current lead-ins situated parallel to the cylinder axis, that extend across the end sections of the cuvette; an upper strip-shaped sheet metal part of said hollow cylindrical cuvette with lateral current lead-ins, comprising a semi-cylindrical bulge, two current lead-ins which extend only over the end portions of the length of the cuvette, and a circular opening at the center of said semi-cylindrical bulge; and a lower strip-shaped sheet metal part of said hollow cylindrical cuvette with lateral current lead-ins, comprising a semi-cylindrical bulge and two current lead-ins which extend over the entire length of the cuvette.

* * * * *